United States Patent [19]
Pilgram et al.

[11] Patent Number: 4,659,858
[45] Date of Patent: Apr. 21, 1987

[54] PREPARATION OF 2,3-DIHYDRO-1,3,2-BENZODIAZAPHOSPHOLE-2-OXIDES

[75] Inventors: Kurt H. Pilgram; Richard D. Skiles, both of Modesto, Calif.

[73] Assignee: Shell Oil Company, Houston, Tex.

[21] Appl. No.: 811,067

[22] Filed: Dec. 19, 1985

[51] Int. Cl.$^4$ .............................................. C07F 9/24
[52] U.S. Cl. ...................................................... 558/81
[58] Field of Search ......................................... 558/81

[56] References Cited
U.S. PATENT DOCUMENTS
3,116,309  12/1963  Pilgram et al. ...................... 558/81

Primary Examiner—Anton H. Sutto
Attorney, Agent, or Firm—Pamela J. McCollough

[57] ABSTRACT

A process for the preparation of 2,3-dihydro-1,3,2-benzodiazaphosphole-2-oxides which comprises reacting 2-nitrodiphenylamine with a trialkyl phosphite at elevated temperature.

3 Claims, No Drawings

PREPARATION OF 2,3-DIHYDRO-1,3,2-BENZODIAZAPHOSPHOLE-2-OXIDES

FIELD OF THE INVENTION

This invention relates to a process for the preparation of 2,3-dihydro-1,3,2-benzodiazaphosphole-2-oxides.

BACKGROUND OF THE INVENTION

It is known that dihydro-1,3,2-benzodiazaphosphole-2-oxides may be prepared by refluxing an addition product of phenylphosphonic dichloride with ortho-diamines in bromobenzene (J. Org. Chem., 26, 3995 (1961)). This method of preparation, however, has certain drawbacks. For example, ortho-diamines are difficult to make and are relatively unstable. Also, the preparative technique utilizing bromobenzene is tedious and often results in poor yields of the desired dihydro-1,3,2-benzodiazaphosphole-2-oxide product.

It was thought that a synthesis involving intramolecular cyclization of nitrenes derived from 2-nitrodiphenylamine derivatives would yield phenazines. Nitrenes are generally obtained by a loss of nitrogen from an azide or by the removal of oxygen from nitroso or nitro compounds. Cyclization of nitrenes derived from 2-nitrophenyl sulfides has led to the formation of phenothiazines. The analogous reaction of a 2-nitrodiphenylamine derivative with excess trialkyl phosphite did not yield the phenazine. Instead, an alternative nitrogen to phosphorous ring closure was achieved leading to the formation of dihydro-1,3,2-benzodiazaphosphole-2-oxide in high yield. This method of preparing dihydro-1,3,2-benzodiazaphosphole-2-oxides is much more efficient than methods previously used.

SUMMARY OF THE INVENTION

This invention relates to a process for preparing 1-alkyl-2-alkoxy-3-aryl-2,3-dihydro-1,3,2-benzodiazaphosphole-2-oxides by treating 2-nitrodiphenylamines with trialkyl phosphites at elevated temperature.

DESCRIPTION OF THE INVENTION

It has been found that 1-alkyl-2-alkoxy-3-aryl-2,3-dihydro-1,3,2-benzodiazaphosphole-2-oxides can be prepared in high yield by treating 2-nitrodiphenylamines with trialkyl phosphites.

The 1-alkyl-2-alkoxy-3-aryl-2,3-dihydro-1,3,2,-benzodiazaphosphole-2-oxides prepared in this invention are defined generally by the formula

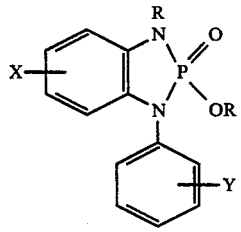
(I)

wherein R is an alkyl containing from one to five carbon atoms and X and Y each represent substituents such as unsubstituted or halogen-substituted alkyl, alkenyl or alkoxy, cyano, alkylsulfonyl, alkoxycarbonyl or halo groups which do not interfere with the reaction.

Compounds of Formula I can be prepared by treating a 2-nitrodiphenylamine

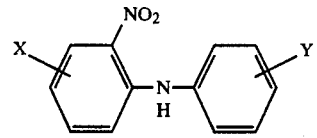

with a trialkyl phosphite, $(RO)_3P$. The trialkyl phosphite is preferably trimethyl phosphite or triethyl phosphite. The 2-nitrodiphenylamine may carry substituents X and Y which may be, for example, unsubstituted or substituted alkyl or alkoxy, as well as other groups not interfering with the reaction. Depending on the nature of the X and Y substituents, trimethyl phosphite may be preferred in one reaction while triethyl phosphite may be preferred in another reaction. The determination of which trialkyl phosphite should be utilized in a given reaction to make the reaction proceed most efficiently can be determined readily by one skilled in the art with a minimal amount of experimentation. Depending on whether trimethyl phosphite or triethyl phosphite is utilized in the reaction, the reaction products formed in addition to the 2,3-dihydro-1,3,2-benzodiazaphosphole-2-oxide are substantially different. In addition, the time required for the reaction to occur as well as the yield of the desired 1-alkyl-2-alkoxy-3-aryl-2,3-dihydro-1,3,2-benzodiazaphosphole-2-oxide product are different for reactions utilizing trimethyl phosphite and reactions utilizing triethyl phosphite. The structure of the products formed in the instant invention was determined by conventional analytical techniques, infrared spectroscopy, mass spectroscopy, and NMR spectroscopy.

The reaction of 2-nitrodiphenylamine with trimethyl phosphite proceeds according to the equation:

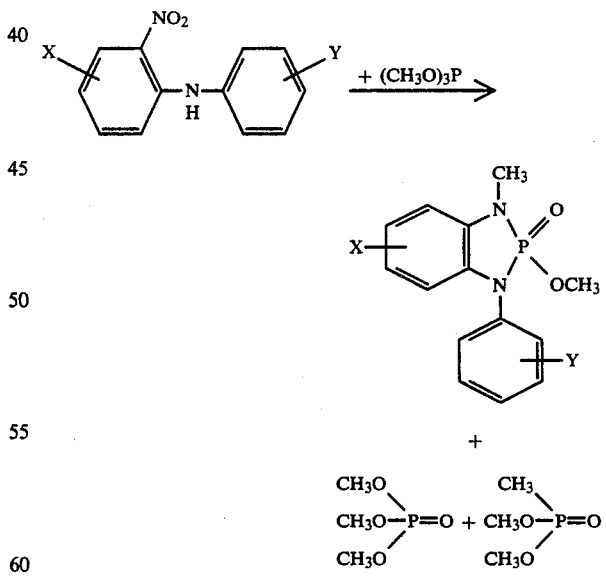

The reaction is carried out at elevated temperature, preferably about 80° C. to about 160° C. The length of time required to complete the reaction is dependent upon the temperature. When the solution of 2-nitrodiphenylamine and trimethyl phosphite is heated to reflux, the reaction proceeds with trimethyl phosphate and dimethyl methyl phosphonate being the only reaction products formed in addition to 1-alkyl-2-alkoxy-3-aryl-2,3-dihydro-1,3,2-benzodiazaphosphole-2-oxide. After a sufficient amount of time has passed for all of the 2-nitrodiphenylamine to react, continued heating at temperatures ranging from about 190° C. to about 210° C. causes rupture of both P—N bonds in Formula I. This eventually results in the conversion of all of the 1-alkyl-2-alkoxy-3-aryl-2,3-dihydro-1,3,2-benzodiazaphosphole-2-oxide to 2-dimethylamino-N-methyldiphenylamine.

By contrast, the reaction of 2-nitrodiphenylamine with triethyl phosphite leads to the formation of a phosporamidate and 2,3-dihydro-1,3,2-benzodiazaphosphole-2-oxide derivative. The reaction proceeds according to the equation:

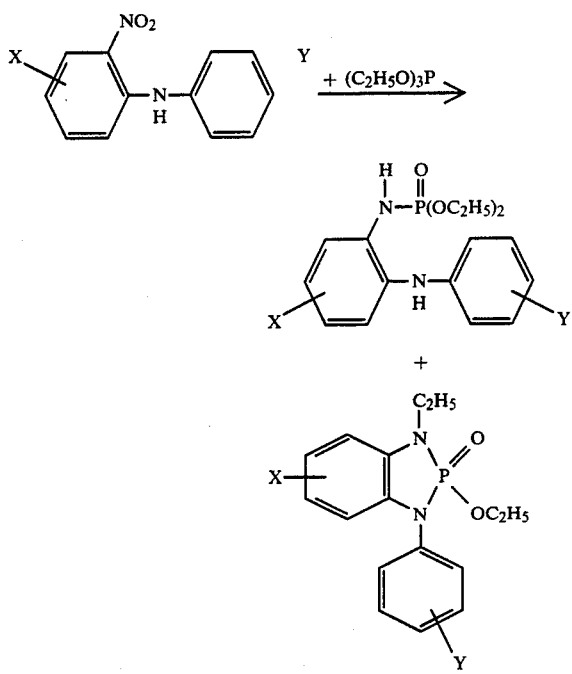

The reaction is carried out at a temperature ranging from about 130° C. to about 165° C. The length of time required for the desired reaction to occur is dependent on temperature and is not critical. When the reaction temperature is maintained at reflux over prolonged periods of time (3–5 days), which is about 180° C. to about 220° C., the products formed are 2-(diethylamino)diphenylamine, 2-(diethylamino)-N-ethyldiphenylamine, and a mixture of tetraethylated ortho-aminodiphenylamines.

Compounds prepared by the process of the invention are suitable for use as intermediates for pharmaceuticals as well as organic ligands such as, for example, a phosphine ligand in a carbonylation reaction.

The invention is further described the by following examples which are intended for illustration and are not to be construed as limiting the invention.

EXAMPLE 1

Preparation of 2,3-dihydro-2-methoxy-3-methyl-1-phenyl-1,3,2-benzodiazaphosphole-2-oxide.

A solution of 10.7 g (0.05 mole) of 2-nitrodiphenylamine in 150 ml of trimethyl phosphite was heated at reflux for 28 hours. The solution was then cooled, poured into 200 ml of aqueous 10% hydrochloric acid and extracted with 3×200 ml of ether. The ethereal extracts were dried (MgSO$_4$), filtered and concentrated under reduced pressure. The residue was purified by silica chromatography to give a syrup, that was crystallized from 1:1 v:v ether:hexane to give 2,3-dihydro-2-methoxy-3-methyl-1-phenyl-1,3,2-benzodiazaphosphole-2-oxide.

EXAMPLE 2

Preparation of 2,3-dihydro-2-ethoxy-3-ethyl-1-phenyl-1,3,2-benzodiazaphosphole-2-oxide.

A solution of 10.7 g (0.05 mole) of 2-nitrodiphenylamine in 50 ml of triethyl phosphite was heated to reflux (160±5° C.). The course of the reaction was monitored by thin layer chromatography. After 5 hours, the reaction was concentrated under rotary evaporation (0.5 mm, 90° C.). The residual oil was then purified by silica chromatography to give a first fraction consisting of red syrup that crystallized from ether to give solid diethyl N-(2-(phenylaminophenyl)phosphoramidate. The second fraction consisted of 2,3-dihydro-2-ethoxy-3-ethyl-1-phenyl-1,3,2-benzodiazaphosphole-2-oxide, an amber red oil.

EXAMPLE 3

Preparation of propionic acid, 2-(4-(2-ethoxy-3-ethyl-2,3-dihydro-2-oxo-5-(trifluoromethyl)-1,3,2-benzodiazaphosphol-1-yl)phenoxy)-, ethyl ester.

A solution of 10.0 g (0.025 mole) of propanoic acid, 2-(4-(2-nitro-4-(trifluoromethyl)phenyl)amino)phenoxy)-, ethyl ester in 50 ml of triethyl phosphite was heated at 150° C. (reflux) for 3 hours until thin layer chromatography showed disappearance of starting material. The mixture was then concentrated under reduced pressure (1 mm, 80° C.). The residue was purified by silica chromatography to yield propionic acid, 2-(4-(2-ethoxy-3-ethyl-2,3-dihydro-2-oxo-5-(trifluoromethyl)-1,3,2-benzodiazaphosphol-1-yl)phenoxy)-, ethyl ester.

We claim as our invention:

1. A process for preparing a compound of the formula

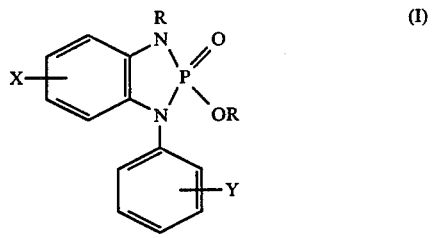

which comprises treating 2-nitro-diphenylamine of the formula

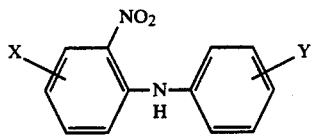

with a trialkyl phosphite (RO)$_3$P, R being an alkyl of up to five carbon atoms, X and Y each representing an unsubstituted or halogen-substituted alkyl, alkenyl or alkoxy, cyano, alkylsulfonyl, alkoxycarbonyl or a halo group at a temperature ranging from about 80° C. to about 165° C.

2. The process of claim 1 wherein the trialkyl phosphite is trimethyl phosphite.

3. The process of claim 1 wherein the trialkyl phosphite is triethyl phosphite.

* * * * *